(12) United States Patent
Oshima et al.

(10) Patent No.: US 7,215,982 B2
(45) Date of Patent: May 8, 2007

(54) METHOD AND DEVICE FOR MEASURING CONCENTRATION OF SPECIFIC COMPONENT

(75) Inventors: Kiyoko Oshima, Shijonawate (JP); Shinji Uchida, Neyagawa (JP); Masahiko Shioi, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 412 days.

(21) Appl. No.: 10/815,687

(22) Filed: Apr. 2, 2004

(65) Prior Publication Data
US 2004/0199060 A1    Oct. 7, 2004

(30) Foreign Application Priority Data
Apr. 3, 2003  (JP) ............................. 2003-100082
Apr. 17, 2003 (JP) ............................. 2003-112944

(51) Int. Cl.
*A61B 5/00* (2006.01)
(52) U.S. Cl. ...................................... 600/310; 600/316
(58) Field of Classification Search ................ 600/309, 600/310, 316, 322
See application file for complete search history.

(56) References Cited
U.S. PATENT DOCUMENTS
6,152,876 A * 11/2000 Robinson et al. ........... 600/322
6,424,849 B1 * 7/2002 Berman et al. ............. 600/316
2003/0143116 A1    7/2003 Zheng et al.

FOREIGN PATENT DOCUMENTS

| EP | 0 967 478 A | 12/1999 |
|---|---|---|
| EP | 0967479 A | 12/1999 |
| JP | 9-113439 | 5/1997 |
| JP | 11-178799 | 7/1999 |
| WO | WO 98/01071 A | 1/1998 |
| WO | WO 02/065090 A2 | 8/2002 |
| WO | WO 03/016882 A1 | 2/2003 |

* cited by examiner

*Primary Examiner*—Eric F. Winakur
(74) *Attorney, Agent, or Firm*—McDermott Will & Emery LLP (57) ABSTRACT

The present invention provides easy and stable measurement of the concentration of a specific component contained in a living body, even when a fluid such as water, saliva or sweat is present between an optical element and the living body or when the measurement is taken at a plurality of measuring parts of a living body. In the measurement of the present invention, a calibration line to be used to correct the influence of a change of a fluid layer present between a living body and an optical element is determined, a measured value is corrected based on the calibration line and the concentration is obtained from the corrected value.

13 Claims, 4 Drawing Sheets

METHOD AND DEVICE FOR MEASURING CONCENTRATION OF SPECIFIC COMPONENT

BACKGROUND OF THE INVENTION

The present invention relates to a method for optically measuring the concentration of a specific component in a living body such as blood sugar level, water or cholesterol by measuring light reflected from the living body and a measuring device using it.

Hitherto, various methods for measuring a sample, a specific component in a living body in particular, with the use of an optical measuring device have been proposed, one of which is a method for measuring blood sugar level by bringing a transparent attenuated total reflectance (ATR) element having a pair of reflecting planes, which are arranged in parallel and facing each other, into contact with top and bottom lips (see Japanese Laid-Open Patent Publications Nos. Hei 9-113439 and Hei 11-178799).

To be more precise, according to the above method, light is introduced into an ATR element made of zinc selenide, silicon, germanium or the like being held in the mouth and pressed against the top and bottom lips. The incident light undergoes repeated total internal reflection between the reflecting planes of the ATR element, each reflecting plane being located at the interface between the lip and the ATR element, and then the light exits the ATR element. Analyzing this exiting light provides information concerning the concentration of a component contained in the lips.

Another proposed method is to introduce a laser beam with a wavelength of 9 to 11 micrometers into an ATR element made of ZnSe optical crystal, which is closely adhered to a mucous membrane of the lips, so as to have multiple reflection inside the ATR element. In this method, attenuated total internal reflection light, scattered reflected light or the like after the multiple reflection is analyzed to determine the blood sugar level or the concentration of ethanol in the blood.

These above methods realize realtime measurement of the concentration of a specific component such as glucose or cholesterol in a noninvasive manner. In these methods, evanescent wave (so-called penetrating wave) is applied to a quantitative analysis.

As described above, by measuring light reflected from a living body, it is possible to acquire information concerning the concentration of a component contained in a body fluid. This method, however, is accompanied by a problem that a fluid present at the interface between the optical element and a living body influences the accuracy of the measurement. It should be noted that the term "information concerning the concentration" includes a concentration itself and an absolute value of concentration as well as a change in concentration with time and the like.

A conventional optical measuring device using such method as described above also has the following problem. Light traveling through an ATR element slightly invades the lips when the light undergoes repeated total internal reflection between the reflecting planes of the ATR element, each reflecting plane being located at the interface between the lip and the ATR element, during which the light is affected by a component contained in a body fluid present at the interface.

Glucose, for example, has an absorption peak at a wavelength of around 1033 $cm^{-1}$ and 1080 $cm^{-1}$. Accordingly, if light having the above wavelength is applied to a living body, the amount of light absorbed will differ according to the concentration of glucose in the living body.

More specifically, in the case of measuring the concentration information of a component in the lips of a living body using an optical element, if a fluid such as saliva is present between the optical element and the lips, the amount of the light reaching the lips will differ according to the thickness of the fluid layer. As a result, the amount of signal to be detected based on the amount of the light varies significantly, giving varying measurement results. Therefore, stable measurement results cannot be obtained.

In the above example, if the concentration information is determined based only on absorption peak values of glucose, erroneous concentration information might be obtained. For example, a low absorbance might be obtained due to a thick saliva layer although, in fact, the living body has a high concentration of glucose. Conversely, a high absorbance might be obtained due to a thin saliva layer although, in fact, the living body has a low concentration of glucose.

Further, a similar problem also occurs when a plurality of living bodies are subjected to the measurement because the amount of the signal varies significantly due to differences in refractive index among individuals.

Furthermore, a similar problem also occurs when the measurement is taken at a body part other than the lips. This is because, if a body fluid such as sweat is present between the measuring part and an optical device, the amount of light reaching the measuring part will differ according to the thickness of the fluid layer, giving varying measurement results.

In the ATR technique, the depth to which evanescent wave penetrates into a measuring object is usually in an order of wavelength. The light penetrates a surface tissue layer extending from the surface of the measuring object to a wavelength order and then returns. The depth of the evanescent wave penetration is determined by a refractive index of the living body and an incident angle of the light entering the optical element.

In the case where a fluid is present between the measuring object and the optical element, a change in the thickness of the fluid present therebetween affects the depth of the evanescent wave penetrating into the measuring object. Likewise, the penetration depth is affected also in the case where a plurality of measuring objects are used for the measurement, because the measuring objects have a different refractive index. Therefore, the above problems are especially obvious in optically measuring devices that utilize an ATR element.

Even in a method using transmitted light, instead of evanescent wave, a fluid exists at the interface between a living body and an optical element. Accordingly, similar to the above, a change in the thickness of the fluid layer affects the wavenumber signal information.

As explained above, conventional measuring methods have a problem that a change in the state of the interface between a living body and the optical element affects the wavenumber signal information. In view of the above problems, the object of the present invention is to provide a method and a device for achieving easy and stable measurement for the concentration of a specific component contained in a living body even when a fluid such as water, saliva or sweat is present between an optical element and a living body or when the measurement is taken at a plurality of measuring parts of a living body.

SUMMARY OF THE INVENTION

In order to solve the above problems, the present invention provides a method for measuring the concentration of a specific component contained in a living body comprising the steps of: (1) introducing light into an optical element, which is absorbed and reflected by a living body in contact with the optical element and then emitted from the optical element; (2) detecting the light emitted from the optical element and obtaining a wavenumber signal from the detected light; (3) correcting the wavenumber signal with the use of a calibration line for correcting the influence of a change in the state of an interface between the living body and the optical element on the wavenumber signal; and (4) obtaining a concentration of a specific component contained in the living body from the corrected wavenumber signal.

The present invention further provides a measuring device for carrying out the above measuring method. The measuring device comprises (a) an optical element to be brought into contact with a living body, (b) a light source for introducing light into the optical element, (c) a light detecting means for detecting the light emitted from the optical element, (d) a signal processing means for processing a wavenumber signal obtained in the light detecting means to correct the wavenumber signal with the use of one or more calibration line(s).

According to the present invention, it is possible to achieve easy and stable measurement of the concentration of a specific component contained in a living body, even when a fluid such as water, saliva or sweat is present between an optical element and a living body or when the measurement is taken at a plurality of measuring parts of a living body.

The present invention relates to a method for measuring the concentration of a specific component contained in a living body comprising the steps of: (1) introducing light into an optical element, which is absorbed and reflected by a living body in contact with the optical element and then emitted from the optical element; (2) detecting the light emitted from the optical element and obtaining a wavenumber signal from the detected light; (3) correcting the wavenumber signal with the use of a calibration line for correcting the influence of a change in the state of an interface between the living body and the optical element on the wavenumber signal; and (4) obtaining a concentration of a specific component contained in the living body from the corrected wavenumber signal.

In the present invention, the calibration curve is created in advance by the steps of: (3a) obtaining "i" different spectrums corresponding to "i" different states of the interface, where the "i" is an integer from 2 to n, and (3b) plotting "i" different points in a coordinate system and connecting the points, each of the "i" different points being determined from "j" different wavenumber signals corresponding to "j" different wavenumbers in each of the "i" different spectrums, where the "j" is an integer from 2 to n. Then, a wavenumber signal obtained from the detected light in the actual measurement is corrected using the calibration line.

It is preferred that the step (3a) is a step of obtaining a first spectrum and a second spectrum corresponding to two different states of the interface and the step (3b) is a step of plotting two points (x1, y1) and (x2, y2) in a coordinate system and connecting the two points to obtain a calibration line, one of the two points (x1, y1) being determined by two different wavenumber signals corresponding to two different wavenumbers in the first spectrum and the other of the two points (x2, y2) being determined by two different wavenumber signals corresponding to two different wavenumbers in the second spectrum.

Advantageously, the step (3) further comprises steps of: preparing a second calibration line having the same inclination as the calibration line and passing through a point, which is determined by wavenumber signals obtained from the detected light at a plurality of different wavenumbers; and converting the wavenumber signal in the step (2) into a corrected wavenumber signal based on the second calibration line and a temporary condition.

Further, in the present invention, the calibration line is created in advance by the steps of: (3A) obtaining "i" different spectrums corresponding to "i" different states of the interface, where the "i" is an integer from 2 to n, while the optical element is in contact with the living body; and (3B) plotting "i" different points in a coordinate system and connecting the points, each of the "i" different points being determined from "j" different wavenumber signals corresponding to "j" different wavenumbers in each of the "i" different spectrums, where the "j" is an integer from 2 to n. Then, a wavenumber signal obtained from the detected light in the actual measurement is corrected using the calibration line.

It is preferred that the step (3A) is a step of obtaining a first spectrum and a second spectrum and the step (3B) is a step of plotting two points (x1, y1) and (x2, y2) in a coordinate system and connecting the two points to obtain a calibration line, one of the two points (x1, y1) being determined by two different wavenumber signals corresponding to two different wavenumbers in the first spectrum and the other of the two points (x2, y2) being determined by two different wavenumber signals corresponding to two different wavenumbers in the second spectrum.

In this case also, it is advantageous that the step (3) further comprises steps of: preparing a second calibration line having the same inclination as the calibration line and passing through a point, which is determined by wavenumber signals obtained from the detected light at a plurality of different wavenumbers; and converting the wavenumber signal in the step (2) into a corrected wavenumber signal based on the second calibration line and a temporary condition.

The change in the state of the interface is preferably a change in the thickness of a fluid layer.

In the preparation of the calibration line, it is advantageous to use wavenumber signals at two or more wavenumbers in the range of 700 to 3200 $cm^{-1}$ and a wavenumber signal at any of the two or more wavenumbers as the temporary condition.

The present invention further relates to a measuring device for carrying out the above-described measuring method. The measuring device is a device for measuring the concentration of a specific component contained in a living body comprising: (a) an optical element to be brought into contact with a living body, (b) a light source for introducing light into the optical element, (c) a light detecting means for detecting the light emitted from the optical element, and (d) a signal processing means for processing a wavenumber signal obtained in the light detecting means to correct the wavenumber signal with the use of one or more calibration line(s).

The signal processing means advantageously stores the calibration line(s) as data.

It is also advantageous that the signal processing means has a function of calculating the calibration line(s).

It is still further advantageous that signal processing means has functions of preparing a second calibration line having the same inclination as the calibration line and passing through a point, which is determined by wavenumber signals obtained from the detected light at a plurality of different wavenumbers, and converting the wavenumber signal in the step (2) into a corrected wavenumber signal based on the second calibration line and a temporary condition.

The calibration line is advantageously a calibration line for correcting the influence of a change in the thickness of a fluid layer present at the interface between the living body and the optical element on the wavenumber signal.

The temporary condition is advantageously a wavenumber signal at any of the two or more wavenumbers in the range of 700 to 3200 $cm^{-1}$ used in the preparation of the calibration line.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
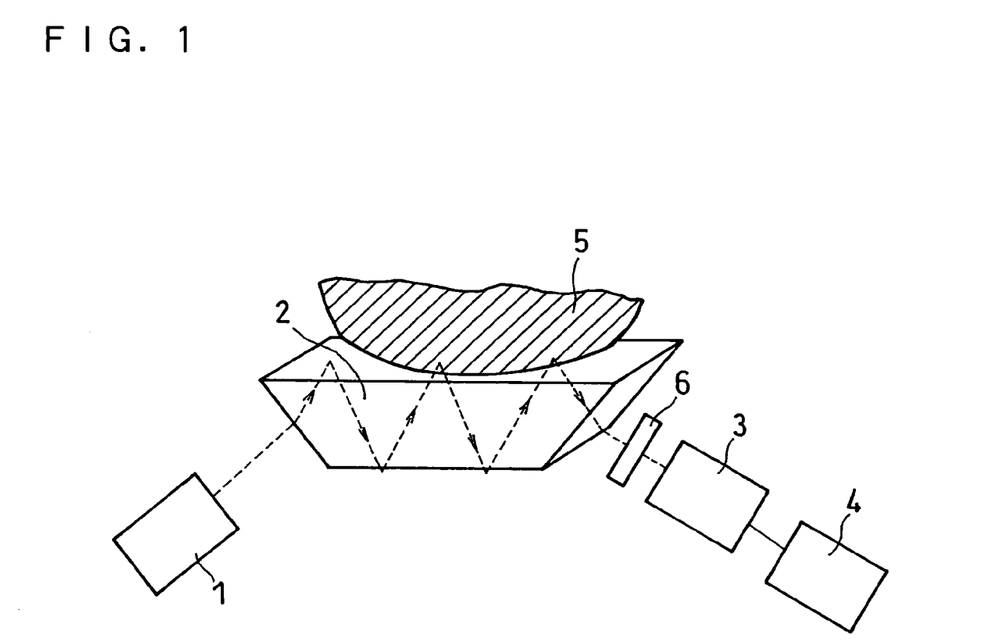
FIG. 1 is a schematic view of a measuring device according to one embodiment of the present invention.
Figure 6:
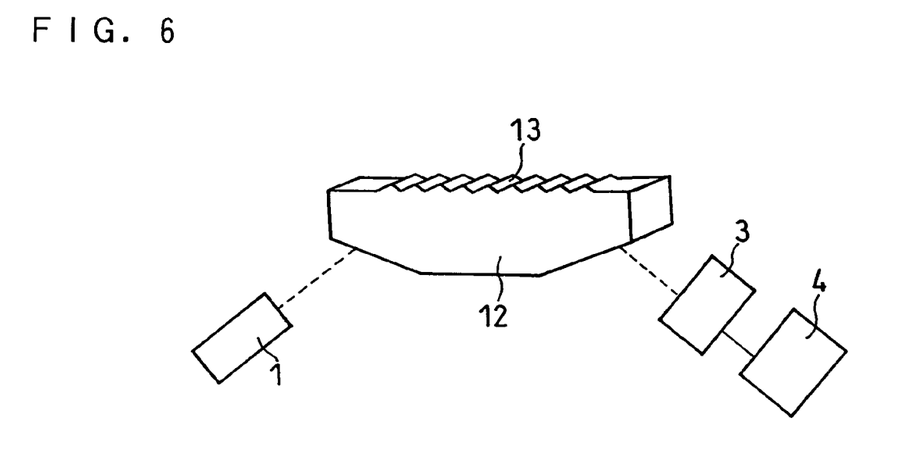
FIG. 6 is a schematic view of a measuring device according to another embodiment of the present invention.

The measuring method and the measuring device in accordance with the present invention are described with reference to the accompanying drawings. FIGS. 1 and 6 respectively show the structure of the measuring device according to one embodiment of the present invention. In these diagrams, light emitted from a light source is shown by a dotted line. It is to be noted that the present invention is not limited to the embodiments.

The measuring method of the present invention involves the following four steps.

Step (1):

In the step (1), after an object to be measured (measuring object) such as a living body is brought into contact with an optical element, light is introduced into the optical element to be absorbed into the living body and reflected, which is then emitted from the optical element.

As seen in FIG. 1, light introduced into an ATR-type optical element 2 from a light source propagates through the optical element 2 by repeated total internal reflection. This light penetrates into a medium such as a living body in contact with the optical element and the penetration depth is several times longer than the wavelength of the light. At this time, an appropriate amount of the penetration wave relative to that of a specific component contained in the measuring object 5 of a living body in close contact with the optical element 2 is absorbed. Subsequently, the light emits from the optical element 2.

In the case of the measuring device shown in FIG. 6, a measuring object 5 of a living body is brought into contact with a substantially V-shaped part 13 formed on the sensing plane of an optical element 12. In this case, the measuring object 5 is partly deformed to fit into the substantially V-shaped part 13. Light introduced into a transmitted light-type optical element 12 from a light source 1 propagates through the optical element 12, during which the light is absorbed into the measuring object 5 and reflected. At this time, an appropriate amount of this light relative to that of a specific component contained in the measuring object 5 is absorbed. Subsequently, the light emits from the optical element 12.

Step (2):

In the step (2), the light emitted from the optical element 2 or 12 is detected by a light detecting means 3, and a wavenumber signal is obtained from the detected light. The wavenumber signal includes an absorbance for a wavenumber, a transmittance and the like.

Step (3):

In the subsequent step (3), the wavenumber signal obtained from the detected light is corrected using a calibration line.

The calibration line is an inclined line based on varying information of the wavenumber signal. To be more precise, the calibration line means data used for correcting the influence of a state change of the interface between the measuring object 5 and the optical element 2 or 12 on the wavenumber signal obtained from the detected light.

The calibration line can be created by the steps of: (3a) obtaining "i" different spectrums corresponding to "i" different states of the interface, where the "i" is an integer from 2 to n; and (3b) plotting "i" different points in a coordinate system and connecting the points, each of the "i" different points being determined from "j" different wavenumber signals corresponding to "j" different wavenumbers in each of the "i" different spectrums, where the "j" is an integer from 2 to n.

A fluid such as water, saliva or sweat or air may be present on the interface. The steps (3a) and (3b) are described with a representative case where the measuring object 5 is the lips, the specific component is glucose and a fluid layer of saliva is present at the interface between the optical element 2 or 12 and the lips.

Figure 2:
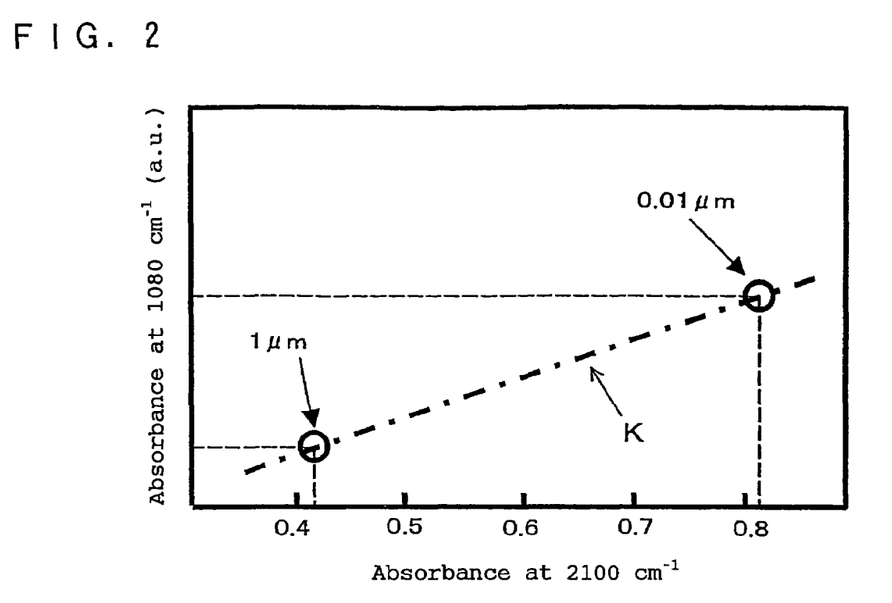
FIG. 2 is a graph whose axes represent absorbances in one embodiment of the present invention.

A calibration line K (i.e. inclined line based on a change of the saliva layer) to be used for correcting the influence of the saliva layer being present between the optical element 2 or 12 and the lips on the wavenumber signal obtained from the detected light is first prepared. It is assumed two different states of the interface are the case where the saliva layer has a thickness of 0.01 µm and the case where the saliva layer has a thickness of 1 µm. FIG. 2 shows a calibration line (absorbance at a wavenumber of 2100 $cm^{-1}$ on the horizontal axis and absorbance at a wavenumber of 1080 cm$^{-1}$ on the vertical axis for a certain glucose concentration) prepared assuming two different cases where the saliva layer has a thickness of 0.01 μm and where the saliva layer has a thickness of 1 μm. The calibration line indicates that the absorbances at an absorption peak of 1080 cm$^{-1}$ differ according to the thickness of the saliva layer even when the same concentration of glucose is used.

In the step (3a), optical information such as a refractive index of the lip as the measuring object 5 of a living body, a refractive index of the optical element 2 or 12, an incident angle of the light entering the optical element 2 or 12 and an internal reflection angle is first specified. Then, a glucose concentration is predetermined, and spectrums in the case of the thickness of the saliva layer being 0.01 μm and the case of the thickness of the saliva layer being 1 μm are determined by calculation.

The requirements for calculating the spectrum should be the same as those used for the actual measurement. The "requirements" herein means a refractive index of the lip, a refractive index of the optical element 2 or 12 used, an incident angle of the light entering the optical element 2 or 12 and the like. In FIG. 2, the glucose concentration is predetermined such that the concentration is corresponded to 80 mg/dl of blood sugar level.

In the subsequent step (3b), the absorbance at a wavenumber of 2100 cm$^{-1}$ is represented by x1 and the absorbance at a wavenumber of 1080 cm$^{-1}$ is represented by y1 in the spectrum in the case of the thickness of the saliva layer being 0.01 μm. At a wavenumber of 2100 cm$^{-1}$, the spectrum shape is greatly affected by the influence of water. At a wavenumber of 1080 cm$^{-1}$, one of the absorption peaks of glucose appears.

Likewise, in the spectrum in the case of the thickness of the saliva layer being 1 μm, the absorbance at a wavenumber of 2100 cm$^{-1}$ is represented by x2 and the absorbance at a wavenumber of 1080 cm$^{-1}$ is represented by y2.

The two points (x1, y1) and (x2, y2) obtained from the above are plotted in a coordinate system (x-y plane) whose horizontal axis describes absorbance at a wavenumber of 2100 cm$^{-1}$ and whose vertical axis describes absorbance at a wavenumber of 1080 cm$^{-1}$. Subsequently, the two points are connected by a straight line to create a calibration line K.

In the above example, the calibration line was created from the calculation of spectrums in the case of the thickness of the saliva layer being 0.01 μm and the case of the thickness of the saliva layer being 1 μm. However, it is also possible that a spectrum is obtained assuming three or more different states of the interface (i.e. saliva layer), and three or more points obtained from the spectrum are connected by a straight line to create a calibration line.

Moreover, in the above example, a pair of absorbances at two different wavenumbers obtained from each spectrum was used as a point for plotting. However, it is also possible that absorbances at three or more different wavenumbers obtained from each spectrum are determined, and coordinates of the three or more absorbances are obtained and used as a point for plotting in a three or more dimensional coordinate system to create a calibration line.

On the whole, a certain material has a specific absorption pattern in the mid-infrared region, and the region in which such absorption peak appears is generally called "fingerprint region". An example thereof is a range of around 650 to 1800 cm$^{-1}$.

Glucose has a lot of large and small absorption peaks in the wavenumber region of 700 to 3200 cm$^{-1}$. Particularly, absorption peaks in the region of 950 to 1550 cm$^{-1}$, which is a finger print region, are mostly used for measuring the concentration of glucose.

When a specimen containing various components such as a living body is used for the measurement, in the finger print region, water affects the absorption peak and other components also affect the absorption peak. Accordingly, the utilization of a wavenumber in that region to correct the influence of water is not preferred because the influence of other components cannot be excluded.

The absorption peak of water appears in the wavenumber region of 1700 to 3000 cm$^{-1}$. It is therefore preferred to use, for the correction, the range of 1700 to 3000 cm$^{-1}$ where the influence of water is very strong, instead of the finger print region. In other words, in the step (3b), it is preferred to use absorbances at least in the wavenumber region of 950 to 1550 cm$^{-1}$ and the region of 1700 to 3000 cm$^{-1}$ for the measurement.

As the refractive index of the measuring object of a living body used for the calculation of the spectrum, a known value may be used or the refractive index may be measured. For example, the refractive index can be determined by the inverse calculation based on the results obtained by measuring the abosorbance of the measuring object of a living body under both P and S-polarized lights. Alternatively, the refractive index can be determined by the inverse calculation based on the results obtained by measuring the absorbance of the measuring object of a living body at two different incident angles. Other methods such as Kramers-Kronig method, Drube method and ellipsometry can also be used.

The process for correcting the wavenumber signal obtained from the detected light with the use of the calibration line obtained above is described. First, as the step (3c), a second calibration line having the same inclination as the above-described calibration line and passing through a point (xm, ym, . . . ) represented by wavenumber signals measured at "j" different wavenumbers used for the preparation of the calibration line data is created.

Subsequently, as the step (3d), a wavenumber signal at at least one wavenumber of said "j" different wavenumbers is designated as a temporary condition. The wavenumber signal as the temporary condition is converted into a wavenumber signal at a wavenumber different from the wavenumber used for the temporary condition to give a corrected wavenumber signal.

The wavenumbers of the measured spectrum to be selected should be the same as those used for the preparation of the calibration line.

The point found by plotting the absorbance at 2100 cm$^{-1}$ on the horizontal axis and that at 1080 cm$^{-1}$ on the vertical axis in the same manner as the above is "s1". The second calibration line having the same inclination as the calibration line K and passing through the point s1 is a calibration line H.

Step (4):

Finally, in the step (4), information concerning the concentration is obtained from the corrected wavenumber signal, which is sent to an external device and outputted.

The case where the correction is made assuming that the saliva layer has a constant thickness of 0.2 μm is explained. When the correction is made assuming that the saliva layer has a constant thickness of 0.2 μm, an absorbance at 2100 cm$^{-1}$ corresponding to that thickness can be calculated in the same manner as in the above step (3a) to give 0.7. The point on the second calibration line H corresponding to 0.7 as the temporary condition is represented by a star-shaped point J.

The absorbance at 1080 cm$^{-1}$ corresponding to the star-shaped point J is represented by R.

The absorbance at 1080 cm$^{-1}$ (i.e. the absorbance at the absorption peak of glucose) of the measured data is represented by P. If 0.7 representing the absorbance at 2100 cm$^{-1}$ is given to the calibration line K representing the change of saliva layer thickness, an absorbance R (i.e. corrected wavenumber signal) will be obtained. In other words, the correction based on the assumption of the saliva thickness being 0.2 μm provides concentration information unaffected by the change of the saliva layer thickness.

In the case where the specific component to be measured is glucose, blood sugar level can be calculated from the corrected measurements with the use of basic information for converting a wavenumber signal at the absorption peak wavenumber of glucose into blood sugar level.

The measurement is preferably repeated a plurality of times at one measuring part of a living body. In the method of the present invention, in order to correct the measured value, the same temporary condition should be used in each measurement. Since the actual measured value is converted into a measured value for a specific temporary condition, it is possible to obtain measured values under the same condition of the interface between the measuring object 5 and the optical element 2 or 12, even if the condition of the interface is changed in each measurement. Thereby, the range of variation in the measured values can be reduced, and stable measurement results can be obtained.

In the method of the present invention, the refractive index of the measuring object 5 is used for the calculation of the spectrum. In the case where the measurement is taken at a different measuring part of a living body, the spectrum can be calculated with the use of a refractive index for that measuring part. Accordingly, the method of the present invention is also applicable to the case where the measurement is taken at a plurality of measuring parts of a living body.

When the measurement is taken at a plurality of measuring parts of a living body, calibration lines corresponding to the measuring parts are necessary because the measured values of all the measuring parts cannot be corrected using only one calibration line. The calibration line corresponding to each of the measuring parts can be created from a spectrum obtained from the calculation with the use of the conditions including the refractive index of each of the measuring parts as described above. The thus-created calibration line is used for the correction of the measured value.

The refractive index of a measuring part used for the calculation of the spectrum may be a known value or may be obtained from measurement when the method of the present invention is carried out.

As described above, in the method of the present invention, it is possible to perform the correction of the measured value even when a plurality of measured parts of a living body are used for the measurement because a calibration line corresponding to each of the measuring parts is used. Accordingly, stable measurement results can be obtained without influence of differences of the measuring parts used.

The calibration line may be created by the steps of: (3A) performing measurement "i" times while the optical element is in contact with the living body to obtain "i" different spectrums corresponding to "i" different states of the interface, where the "i" is an integer from 2 to n,; and (3B) plotting "i" different points in a coordinate system and connecting the points, each of the "i" different points being determined from "j" different wavenumber signals corresponding to "j" different wavenumbers in each of the "i" different spectrums, where the "j" is an integer from 2 to n.

In the step (3A), with one touch of an operation switch or the like, data immediately after the start of the measurement and data after a certain period of time are automatically collected. The "certain period of time" can be appropriately adjusted. The former data and the latter data may be collected in a row. Alternatively, a certain period of time, i.e. several seconds to several minutes, may be allowed between the collection of the former data and that of the latter data. What is important in this step is to successively collect at least two measured data while the optical element 2 or 12 is in contact with the measuring object 5.

Further, in the step (3A), two or more measured data can be colleted by one operation. A calibration line having more accurate inclination can be obtained with more frequent measurement and more data.

Figure 4:
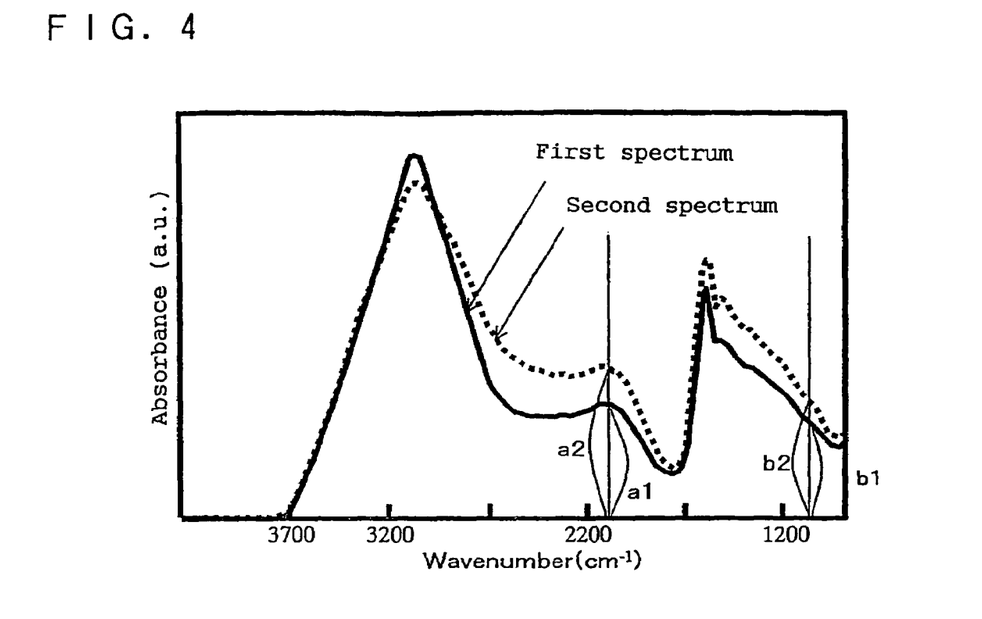
FIG. 4 is a graph showing spectrums obtained after the measurement of a specific component in one embodiment of the present invention.

In the subsequent step (3B), as seen from FIG. 4, the absorbance at 2100 cm$^{-1}$ is represented by "a1" and that at 1080 cm$^{-1}$ is represented by "b1" in the spectrum obtained from the first data. Likewise, the absorbance at 2100 cm$^{-1}$ is represented by "a2" and that at 1080 cm$^{-1}$ is represented by "b2" in the spectrum obtained from the second data.

Figure 5:
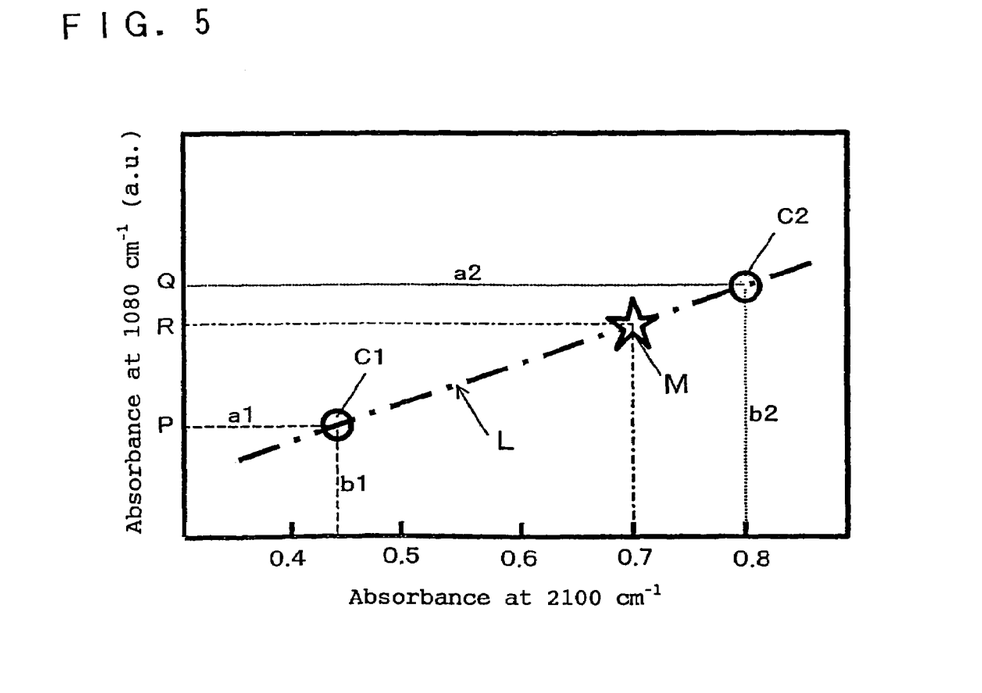
FIG. 5 is a graph used for explaining a process of making the correction in another embodiment of the present invention.

The thus-obtained two points (a1, b1) and (a2, b2) are plotted in an x-y plane whose horizontal axis describes absorbance at 2100 cm$^{-1}$ and whose vertical axis describes absorbance at 1080 cm$^{-1}$, as shown in FIG. 5. A calibration line L can be obtained by connecting the two points C1 and C2 with a straight line.

Although, in the above example, the calibration line was created from two different measured data, it may be created by first obtaining not less than two spectrums and then connecting three or more points obtained from the spectrums. As stated earlier, the calibration line can also be created by determining absorbances at three or more different wavenumbers obtained from each of the spectrums to give the coordinates of the three or more points, which is then plotted in a three or more dimensional coordinate system.

In the previously described step (4), when the specific component to be measured is glucose, blood sugar level can be calculated from the corrected measurement values with the use of basic information for converting a wavenumber signal at the absorption peak wavenumber of glucose into blood sugar level.

Now, the measuring device for carrying out the measuring method of the present invention is again explained with reference to FIG. 1. As shown in FIGS. 1 or 6, the measuring device in accordance with the present invention comprises a light source 1, an optical element 2 or 12, a light detecting means 3, a signal processing means 4, a polarizer 6, a spectroscopic means (not shown in the figures) placed between the light source 1 and the optical element 2. It further comprises a program for performing the functions of the measuring device and a recording medium for storing the program.

The light source 1 can be any light source that emits light having the same wavenumber as that of the absorption peak of a specific component to be measured. Examples thereof include a globar light source which is a sintered silicon carbide (SiC) rod, a $CO_2$ laser and a tungsten lamp.

As the materials for the optical elements 2 and 12, any material known in the relevant field can be used. Examples thereof include Si, Ge, SiC, diamond, ZnSe, ZnS and KrS.

In the case of measuring a component having absorption peaks at the wavenumbers of 1033 and 1080 cm$^{-1}$ in the infrared region, such as glucose, the optical element is preferably made of germanium or silicon having less amount of impurities such as boron and phosphorus and a resistivity of not less than 100 Ωcm, more preferably a resistivity of not less than 1500 Ωcm because the germanium and the silicon have a high transmittance in the infrared wavelength of about 9 to 10 μm.

As the light detecting means 3, any means known in the relevant field can be used. Examples thereof include a pyroelectric sensor and an MCT detector.

The signal processing means 4 may be any device that can correct a wavenumber signal from light detected at the light detecting means with the use of the calibration line data. For example, a calculator can be used as the signal processing means.

When an object to be measured is previously specified, the signal processing means 4 may previously contain or store standard calibration lines determined by calculation. Alternatively, a standard calibration line may be created by calculation every time the measurement is performed.

In the case of using a plurality of living bodies or a plurality of measuring parts of a living body for the measurement, the signal processing means 4 may contain a plurality of standard calibration lines prepared based on different refractive indices and different optical angles of the measuring object 5 and the optical element 2 or 12, and select a standard calibration line suitable for the measuring object and optical element to be used.

Further, in the signal processing means 4, the refractive index of the measuring object 5 may be determined and the spectrum may be calculated using the refractive index. In this case, the calibration line data is produced for each measuring object in the signal processing means. The refractive index is determined by calculation of the results obtained by measuring two types of polarized lights, i.e. P-polarized light and S-polarized light, of the measuring object 5 of a living body with the use of the polarizer 6 that polarizes the light.

In the case where the specific component is glucose, the signal processing means 4 may convert the corrected absorbance into blood sugar level based on basic information for converting the absorbance at the absorption peak wavenumber of glucose into blood sugar level that has been stored in the signal processing means 4, which is then passed to an external device.

The polarizer 6 may be any polarizer known in the relevant field. Examples thereof include a wire-grid polarizer, a prism polarizer, a dielectric prism polarizer, a film polarizer and a reflection polarizer.

The specific component may be any material in a living body that can be optically measured. Examples thereof include blood sugar, water, cholesterol, neutral fat, lactic acid, ethanol in blood and various components in body fluids.

The measuring object 5 may be anything that contains the material that can be optically measured. Examples thereof include tissues of a living body such as skin and lip. Particularly, lip is preferred because the lip has a fluid layer thereon, which makes contact with the optical element 2 or 12 easy.

The concentration information includes an absolute value of the concentration, a component ratio, a composition of the specific component to be measured and their changes with time.

Since the measuring device in accordance with the present invention further comprises a spectroscopic means, it is possible to determine the wavelength dependency of absorption of the specific component contained in a living body.

The use of the FT-IR technique with an interferometer is preferable because it enables measurement with high sensitivity.

When the specific component is glucose having absorption peaks at the wavenumbers of 1033 and 1080 cm$^{-1}$ in the infrared region, a globar light source is preferably used as the light source. This is because the globar light source can cover a relatively wide wavelength range and emit light efficiently even in a long wavelength range of about 10 μm.

The optical element 2 or 12 is preferably made of germanium or silicon having less amount of impurities such as boron and phosphorus and a resistivity of not less than 100 cm because the germanium and the silicon have a high transmittance in the infrared wavelength of about 9 to 10 μm. More preferably, the resistivity is not less than 1500 cm. The polarizer is preferably a wire-grid polarizer.

By virtue of the measuring device in accordance with the present invention having the structure as described above, easy measurement of the concentration of a specific component can be achieved in any of the following cases: (i) where the measurement is taken at one measuring part of one living body; (ii) where the measurement is taken at a plurality of measuring parts of one living body; and (iii) where the measurement is taken at one measuring part of a plurality of living bodies (i.e. one measuring part for one living body); and (iv) where the measurement is taken at a plurality of measuring parts of a plurality of living bodies (i.e. a plurality of measuring parts for one living body).

The measuring device in accordance with the present invention may further comprise a program that allows a computer to perform all or some of the functions of the measuring device. The program is run by the computer.

Additionally, the program may be stored in a recording medium. The recording medium carries the program that allows a computer to perform all or some of the functions of the measuring device of the present invention. The program should be readable by a computer. The program having read by the computer is run by the computer to carry out the functions. The term "some of the functions" means one or some means of all of the plurality of means.

As a preferred implementation of the program, the program is recorded in a recording medium readable by a computer, which is run by the computer.

Alternatively, the program may be transmitted through a transport medium to a computer so that the computer reads the program and runs it.

Examples of the form of the data include database or data format. An example of the recording medium is a ROM. Examples of the transport medium include transport media such as the Internet, light, radio wave and sound wave.

The computer may contain not only hardware such as a CPU but also firmware, OS and peripheral devices.

As described above, the advantages of the present invention may be realized by software or by hardware.

EXAMPLE 1

Figure 3:
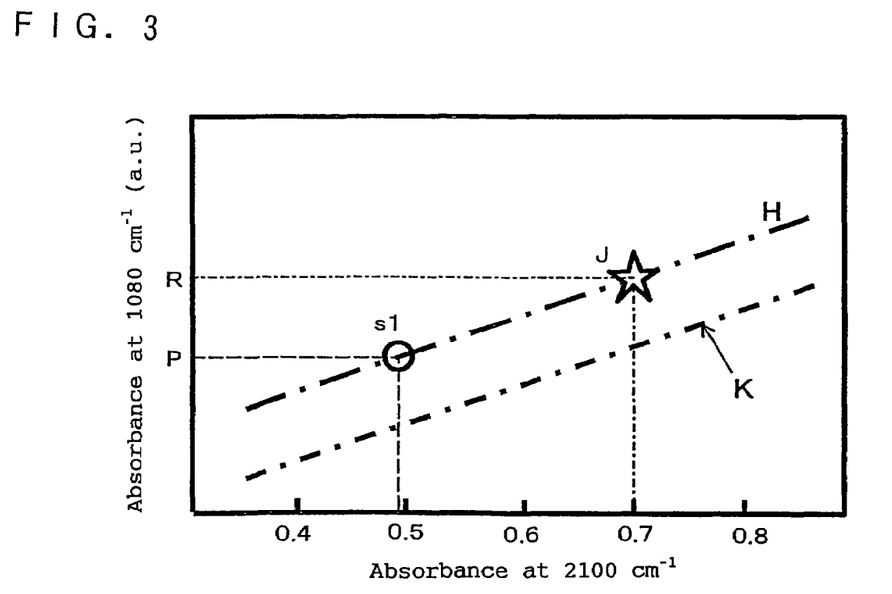
FIG. 3 is a graph used for explaining a process of making the correction in one embodiment of the present invention.

In this example, with the use of a measuring device shown in FIG. 1, the concentration of glucose was measured by the measuring method in accordance with the present invention. FIG. 3 is a graph used for explaining the process for correcting the wavenumber signal of glucose.

The measurement of this example was taken at lips as the measuring object 5. The wavenumbers used for preparing a calibration line K were 2100 cm$^{-1}$ and 1080 cm$^{-1}$.

The measuring device used in this example included an SiC light source as the light source 1, a germanium ATR element as the optical element 2, a pyroelectric sensor as the light detecting means 3 and a calculator as the signal processing means 4. Although not shown in the figure, a spectroscopic means was placed between the light source 1 and the ATR element 2.

Spectrum measurement was performed as follows. First, the lips as the measuring object 5 were made contact with the ATR element 2 of the measuring device. Then, light was introduced into the ATR element 2 at a certain incident angle. Light emitted from the ATR element was detected by the pyroelectric sensor 3, and thus a measured spectrum including a wavenumber signal was obtained.

Subsequently, in the calculator 4, absorbances at the same wavenumbers as used in the preparation of the calibration line K (i.e. absorbances at 2100 $cm^{-1}$ and 1080 $cm^{-1}$) were determined from the measured spectrum data received from the pyroelectric sensor 3. The absorbances at 2100 $cm^{-1}$ and 1080 $cm^{-1}$ were plotted as shown in FIG. 3. The point specified by the absorbances of 2100 $cm^{-1}$ and 1080 $cm^{-1}$ was referred to as a point "s1". A second calibration line H passing through the point s1 and parallel to the calibration line K, which is to be used for the correction, was obtained. In other words, a change in the thickness of the saliva layer was estimated from a line plotted by shifting the inclined calibration line K representing the change in the saliva layer to a point s1 of the measured data.

In this example, correction was made on the assumption of the saliva layer having a constant thickness of 0.2 µm. The absorbance at 2100 $cm^{-1}$ for this thickness was calculated, in the same manner as when the calibration line K was obtained, to give 0.7. The point on the second calibration line H corresponding to 0.7 as the temporary value was represented by a star-shaped point J, and the absorbance at 1080 $cm^{-1}$ indicated by the star-shaped point J was represented by R.

In the measured data, the absorbance at 1080 $cm^{-1}$, (i.e. the absorbance at the absorption peak of glucose) was represented by P. An absorbance at 2100 $cm^{-1}$ of 0.7 was given to the calibration line K representing the change of saliva layer thickness to find an absorbance R, that is, a corrected wavenumber signal. The thus-obtained absorbance R was passed to an external device and outputted.

Such measurement was repeated several times at one site of the lips as the measuring object 5. Throughout the repeated measurement, the temporary condition was set to 0.7, that is, the absorbance at 2100 $cm^{-1}$. The measured values obtained by the repeated measurement exhibited a small range of variation. Therefore, it was clear that the present invention provided more stable measurement results.

Although, in this example, an absorbance at 2100 $cm^{-1}$ of 0.7 was used as the temporary condition for determining an abosorbance at 1080 $cm^{-1}$ corresponding to the star-shaped point J in FIG. 3, the present invention is not limited to the above. The wavenumber may be, for example, other wavenumber susceptible to water except 2100 $cm^{-1}$. Further, in order to temporarily obtain a saliva layer thickness of 0.2 µm, the absorbance at 2100 $cm^{-1}$ was set to 0.7, but the absorbance at 2100 $cm^{-1}$ is not limited to this value. Likewise, the saliva layer thickness is not limited to 0.2 µm.

Figure 7:
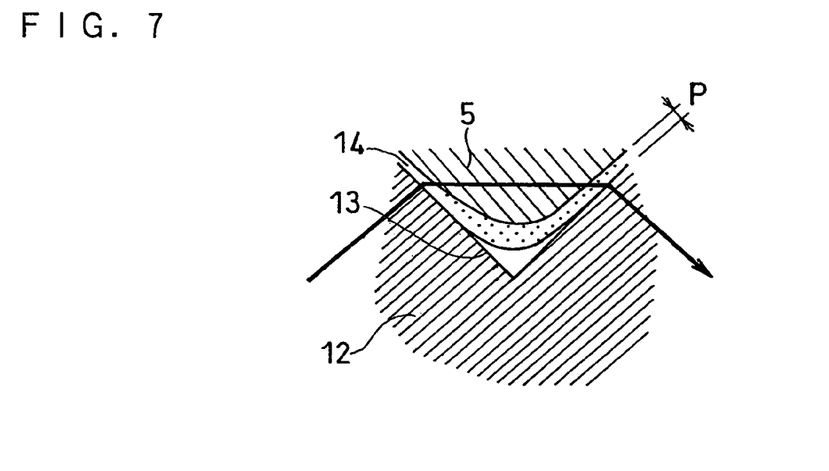
FIG. 7 is an enlarged cross sectional view illustrating a state between a measuring object and a measuring device according to one embodiment of the present invention.

Meanwhile, in spectrum measurement using the measuring device shown in FIG. 6, the lips, for example, as the measuring object 5 was brought into contact with the optical element 12. As shown in FIG. 7, the measuring object 5 was fitted into the substantially V-shaped part 13 of the optical element 12 with the saliva layer 14 interposed between the measuring object 5 and the optical element 12. Light was introduced thereinto from the light source 1. An appropriate amount of the light relative to that of the specific component of the measuring object 5 was absorbed and the light was emitted from the optical element 12. Subsequently, a second calibration line H parallel to the calibration line was created and the temporary condition was given thereto as described above to make the correction.

Because the saliva layer present between the measuring object 5 and the optical element 2 or 12 had a different thickness every time the measurement was taken, the amount of the light reaching the measuring object 5 differed, causing the absorbances to have a wide range of variation. It has been considered difficult to maintain the thickness of the saliva layer constant. However, in the present invention, a standard relation between the absorbance at the absorption peak wavenumber of glucose and the thickness of the saliva layer present between the optical element 2 or 12 and the measuring object 5 was determined in advance by calculation. With the use of this relation for the correction, the actual measured value was converted into an absorbance on the assumption of the saliva layer having a predetermined constant thickness.

This always provides an absorbance based on the assumption that the saliva layer thickness during the measurement is constant. Since the range of variation in the measured results is reduced, it is possible to achieve measurement that always yields stable measured values.

In this example, lip was used as the measuring object 5 and saliva as the varying factor to be used for the correction, but the measuring object 5 may be skin and the varying factor may be sweat.

EXAMPLE 2

In this example also, the concentration of glucose was measured using the measuring method of the present invention and the measuring device shown in FIG. 1.

FIG. 4 shows two spectrums obtained from the first and second measurement carried out successively while the lip as the measuring object 5 was kept in contact with the ATR element 2. The thickness of the saliva layer gradually varied while the measuring object 5 was kept in contact with the ATR element 2 and thus the amount of the light reaching the lip differed, in other words, the signal information at the first and second measurement differed. For this reason, two different spectrums were obtained.

Then, the point represented by the absorbance a1 at 2100 $cm^{-1}$ and the absorbance b1 at 1080 $cm^{-1}$ in the first spectrum was referred to as "C1", and the point represented by the absorbance a2 at 2100 $cm^{-1}$ and the absorbance b2 at 1080 $cm^{-1}$ in the second spectrum was referred to as "C2". As shown in FIG. 5, the two points were connected by a straight line to give a calibration line L.

An absorbance at 2100 $cm^{-1}$ of 0.7 as the temporary condition was given to the calibration line L, and the absorbance at 1080 $cm^{-1}$ (shown by the star-shaped point M in FIG. 5) was calculated. Such measurement was repeated several times. Throughout the repeated measurement, the temporary condition was set to an absorbance at 2100 $cm^{-1}$ of 0.7.

The measured values obtained from the above measurement had a smaller range of variation. It was evident from this that the present invention provided stable measurement results.

Although, in this example, an absorbance at 2100 $cm^{-1}$ of 0.7 was used as the temporary condition for determining a value shown by the star-shaped point M, the present invention is not limited to the above.

The absorbance at 1080 cm$^{-1}$ (i.e. the absorbance at the absorption peak of glucose) of the first data was P and the absorbance at 1080 cm$^{-1}$ of the second data was Q.

The temporary condition (i.e. an absorbance at 2100 cm$^{-1}$ of 0.7) was given to the calibration line L to find an absorbance R at the absorption peak wavenumber of glucose (i.e. at 1080 cm$^{-1}$) as a corrected wavenumber signal.

Likewise, with the use of the measuring device shown in FIG. 6, the measurement was carried out successively twice while the measuring object 5 was kept in contact with the optical element 12 to give the first and second spectrums.

Figure 8:
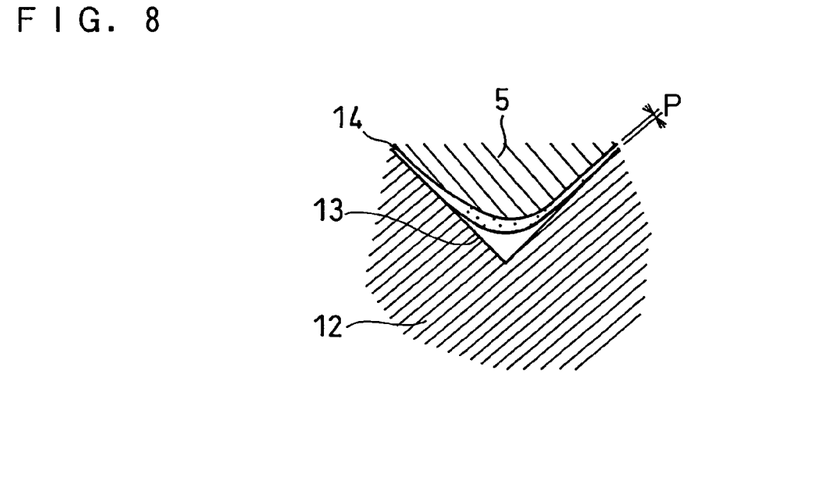
FIG. 8 is an enlarged cross sectional view illustrating another state between a measuring object and a measuring device according to one embodiment of the present invention.

FIGS. 7 and 8 show the state between the substantially V-shaped part 13 of the optical element 12 and the thickness P of the saliva layer 14 of the measuring object 5. During the measurement, as seen from FIGS. 7 and 8, the thickness P of the saliva layer 14 varied because saliva was gradually shifted to the outside as the lip as the measuring object 5 was brought into closer contact with the substantially V-shaped part 13. Because of this, the wavenumber signals at the first and second measurement differed, and two different spectrums were obtained.

Then, the correction was carried out by determining a second calibration line L and giving the temporary condition mentioned above to the second calibration line L.

In EXAMPLEs 1 and 2, actual change in the thickness of the saliva layer present between the optical element 2 or 12 and the lip as the measuring object 5 was utilized for the correction. Specifically, an absorbance for the predetermined saliva layer thickness was estimated from actual measured value based on the calibration line L obtained from the thickness change. Thereby, information on the assumption of the saliva layer having a constant thickness during the measurement was obtained, reducing the range of variation of the measurement.

Additionally, lip was used as the measuring object 5 and saliva as the varying factor to be used for the correction, but the measuring object 5 may be skin and the varying factor may be sweat.

In EXAMPLEs described above, the measuring method of the present invention was carried out based on an absorbance at 2100 cm$^{-1}$ and an absorbance at 1080 cm$^{-1}$, that is, one of the absorption peaks of glucose, but there may be used information, for example, obtained by baseline-correcting a plurality of wavenumber signals.

As described above, according to the present invention, easy and stable measurement of the concentration of a specific component contained in a measuring part of a living body can be achieved even when a fluid such as water, saliva or sweat is present between an optical element and the living body or when the measurement is taken at a plurality of measuring parts of a living body.

According to the measuring method and the measuring device in accordance with the present invention, it is possible to achieve easy and stable measurement of the concentration of a specific component contained in a living body, even when a fluid such as water, saliva or sweat is present between an optical element and the living body or when the measurement is taken at a plurality of measuring parts of a living body. Therefore, the present invention is useful in the measurement of a component of a body fluid for medical purpose.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

The invention claimed is:

1. A method for measuring the concentration of a specific component contained in a living body comprising the steps of:
   (1) introducing light into an optical element, which is absorbed and reflected by a living body in contact with said optical element and then emitted from said optical element:
   (2) detecting the light emitted from said optical element and obtaining a wavenumber signal from the detected light:
   (3) correcting said wavenumber signal with the use of a calibration line for correcting the influence of a change in the state of an interface between said living body and said optical element on said wavenumber signal,
   (4) obtaining the concentration of the specific component contained in said living body from the corrected wavenumber signal; and
   (5) outputting the concentration of the specific component,
   wherein said calibration line is prepared by the steps of:
      (3a) obtaining "i" different spectrums corresponding to "i" different states of said interface, where said "i" is an integer from 2 to n; and
      (3b) plotting "i" different points in a coordinate system and connecting said points to obtain a calibration line, each of said "i" different points being determined from "j" different wavenumber signals corresponding to "j" different wavenumbers in each of said "i" different spectrums, where said "j" is an integer from 2 to n.

2. The method for measuring the concentration of the specific component in accordance with claim 1, wherein
   said step (3a) is a step of obtaining a first spectrum corresponding to a first state of said interface and a second spectrum corresponding to a second state of said interface, and
   said step (3b) is a step of plotting two points (x1, y1) and (x2, y2) in a coordinate system and connecting said two points to obtain a calibration line, one of said two points (x1, y1) being determined in said first spectrum by a first wavenumber signal x1 at a first wavenumber whose signal varies depending on a state of said interface and a second wavenumber signal y1 at a second wavenumber whose signal varies depending on a concentration of said specific component and the other of said two points (x2, y2) being determined in said second spectrum by a third wavenumber signal x2 at said first wavenumber and a fourth wavenumber signal y2 at said second wavenumber.

3. The method for measuring the concentration of the specific component in accordance with claim 2, wherein said step (3) further comprises steps of:
   preparing a second calibration line having the same inclination as said calibration line and passing through a third point (x3, y3), which is determined by a fifth wavenumber x3 obtained from said detected light at said first wavenumber and a sixth wavenumber signal y3 obtained from said detected light at said second wavenumber; and
   converting a seventh wavenumber signal at said first wavenumber obtained when the state of said interface is assumed to be in a temporary condition into an eighth wavenumber signal at said second wavenumber based on said second calibration line.

4. The method for measuring the concentration of the specific component in accordance with claim 3, wherein the preparation of said calibration line involves the use of wavenumber signals at two or more wavenumbers in the range of 700 to 3200 cm$^{-1}$.

5. The method for measuring the concentration of the specific component in accordance with claim 1 wherein said change in the state of said interface means a change in the thickness of a fluid layer.

6. A method for measuring the concentration of a specific component contained in a living body comprising the steps of:
(1) introducing light into an optical element, which is absorbed and reflected by a living body in contact with said optical element and then emitted from said optical element;
(2) detecting the light emitted from said optical element and obtaining a wavenumber signal from the detected light;
(3) correcting said wavenumber signal with the use of a calibration line for correcting the influence of a change in the state of an interface between said living body and said optical element on said wavenumber signal;
(4) obtaining the concentration of the specific component contained in said living body from the corrected wavenumber signal; and
(5) outputting the concentration of the specific component,
wherein said calibration line is prepared by the steps of:
(3A) obtaining "i" different spectrums corresponding to "i" different states of said interface, where said "i" is an integer from 2 to n, while said optical element is in contact with said living body; and
(3B) plotting "i" different points in a coordinate system and connecting said points to obtain a calibration line, each of said "i" different points being determined from "j" different wavenumber signals corresponding to "j" different wavenumbers in each of said "i" different spectrums, where said "j" is an integer from 2 to n.

7. The method for measuring the concentration of the specific component in accordance with claim 6, wherein
said step (3A) is a step of obtaining a first spectrum corresponding to a first state of said interface and a second spectrum corresponding to a second state of said interface, and
said step (3B) is a step of plotting two points (x1, y1) and (x2, y2) in a coordinate system and connecting said two points to obtain a calibration line, one of said two points (x1, y1) being determined in said first spectrum by a first wavenumber signal x1 at a first wavenumber whose signal varies depending on a state of said interface and a second wavenumber signal y1 at a second wavenumber whose signal varies depending on a concentration of said specific component and the other of said two points (x2, y2) being determined in said second spectrum by a third wavenumber signal x2 at said first wavenumber and a fourth wavenumber signal y2 at said second wavenumber.

8. The method for measuring the concentration of the specific component in accordance with claim 7, wherein said step (3) further comprises steps of:
preparing a second calibration line having the same inclination as said calibration line and passing through a third point (x3, y3), which is determined by a fifth wavenumber x3 obtained from said detected light at said first wavenumber and a sixth wavenumber signal y3 obtained from said detected light at said second wavenumber; and
converting a seventh wavenumber signal at said first wavenumber obtained when the state of said interface is assumed to be in a temporary condition into an eighth wavenumber signal at said second wavenumber based on said second calibration line.

9. The method for measuring the concentration of the specific component in accordance with claim 6, wherein said change in the state of said interface means a change in the thickness of a fluid layer.

10. A device for measuring the concentration of the specific component contained in a living body comprising:
(a) an optical element adapted to be brought into contact with a living body;
(b) a light source for introducing light into said optical element;
(c) a light detecting means for detecting the light emitted from said optical element; and
(d) a signal processing means for processing a wavenumber signal obtained in said light detecting means to correct said wavenumber signal with the use of one or more calibration line(s), wherein said signal processing means
(1) memorizes a first calibration line comprising:
a first point (x1, y2) determined in a first spectrum obtained when an interface between said living body and said optical element is in a first state by a first wavenumber signal x1 at a first wavenumber whose signal varies depending on a state of said interface and a second wavenumber signal y1 at a second wavenumber whose signal varies depending on a concentration of said specific component, and
a second point (x2, y2) determined in a second spectrum obtained when the interface between said living body and said optical element is in a second state by a third wavenumber signal x2 at said first wavenumber and a fourth wavenumber signal y2 at said second wavenumber;
(2) prepares a second calibration line having the same inclination as said first calibration line and passing through a third point (x3, y3), which is determined by a fifth wavenumber x3 obtained from said detected light at said first wavenumber and a sixth wavenumber signal y3 obtained from said detected light at said second wavenumber;
(3) converts a seventh wavenumber signal at said first wavenumber obtained when the state of said interface is assumed to be in a temporary condition into an eighth wavenumber signal at said second wavenumber based on said second calibration line; and
(4) calculates the concentration of said specific component based on said eighth wavenumber signal.

11. The device for measuring the concentration of the specific component in accordance with claim 10, wherein said signal processing means calculates said first calibration line.

12. The device for measuring the concentration of the specific component in accordance with claim 10, wherein a fluid layer is present at said interface.

13. The device for measuring the concentration of the specific component in accordance with claim 10, wherein said first wavenumber and said second wavenumber are wavenumbers selected from 700 to 3200 cm$^{-1}$.

* * * * *